United States Patent [19]

Bryson

[11] 4,229,415

[45] Oct. 21, 1980

[54] INDUSTRIAL DEODORIZER

[75] Inventor: John D. Bryson, Milwaukee, Wis.

[73] Assignee: Will Ross, Inc., Milwaukee, Wis.

[21] Appl. No.: 914,422

[22] Filed: Jun. 12, 1978

[51] Int. Cl.² .................... A01M 19/00; A61L 9/01; A61L 9/02

[52] U.S. Cl. ................................ 422/109; 43/129; 239/34; 239/57; 261/DIG. 17; 261/DIG. 65; 312/31.3; 422/111; 422/116; 422/124; 422/125; 422/305; 422/306

[58] Field of Search ............... 422/4, 5, 109, 110, 422/111, 116, 119, 124, 125, 305, 306; 261/DIG. 17, DIG. 65; 424/76; 239/34, 55–57; 43/129; 128/187; 312/31.2, 31.3

[56] References Cited

U.S. PATENT DOCUMENTS

| 2,087,436 | 7/1937 | Kirby | 422/4 |
|---|---|---|---|
| 2,686,944 | 8/1954 | Gubelin | 422/116 |
| 2,937,419 | 5/1960 | Vaughn | 422/119 |
| 3,055,066 | 9/1962 | Duncan | 422/124 |
| 3,418,068 | 12/1968 | Gilbertson | 422/124 |
| 3,634,053 | 1/1972 | Klass et al. | 261/DIG. 17 |
| 3,711,023 | 1/1973 | Smith | 239/55 |
| 3,885,737 | 5/1975 | Watkins | 239/34 |
| 3,895,928 | 7/1975 | Morgan | 422/119 |
| 3,908,905 | 9/1975 | Von Philipp et al. | 239/55 |
| 4,102,656 | 7/1978 | Koritz | 422/306 |

Primary Examiner—Bradley R. Garris
Attorney, Agent, or Firm—Michael, Best & Friedrich

[57] ABSTRACT

A dispenser comprising a rectangular housing defining an air inlet chamber between the first partition and the top wall of the housing, a valved air inlet communicating with the air inlet chamber, a second partition defining an air outlet chamber between the second partition and the bottom wall of the housing and a central chamber between the first and second partitions, a valved air outlet communicating with the air outlet chamber, apertures in the first and second partitions for affording air flow from the air inlet chamber, at least one tray member, a support on the end walls for horizontally supporting the tray member in the central chamber and for facilitating at least partial withdrawal of the tray member, a holder on the tray member for removably holding a plurality of relatively thin rectangular envelopes which contain a substance to be dispensed and which are arranged in parallel vertical relation to each other to permit air flow past the envelopes from the air inlet chamber to the air outlet chamber, and a blower in one of the air inlet and air outlet chambers for inducing air flow from the air inlet chamber to the central chamber and from the central chamber to the air outlet chamber.

20 Claims, 2 Drawing Figures

INDUSTRIAL DEODORIZER

BACKGROUND OF THE INVENTION

The invention relates to dispensers for delivering a substance, such as odorants and deodorants. More particularly, the invention relates to dispensers for commercial and industrial use. Still further, the invention relates to stationary as well as portable dispensers.

SUMMARY OF THE INVENTION

The invention provides a dispenser comprising a rectangular housing including interconnected top and bottom walls, opposed front and back walls, opposed first and second end walls, door means in the front wall for providing an access opening which can be opened and closed, a first partition extending in spaced relation to the top wall and between the end walls and between the front and back walls to define an air intake chamber between the first partition and the top wall, air inlet means communicating with the air inlet chamber, a second partition extending in spaced relation to the bottom wall and in generally parallel relation to the first partition and between the end walls and between the front and back walls to define an air outlet chamber between the second partition and the bottom wall and to define a central chamber between the first and second partitions, air outlet means communicating with the air outlet chamber, aperture means in the first and second partitions for affording air flow from the air inlet chamber to the central chamber and from the central chamber to the air outlet chamber, at least one tray member, means on the end walls for horizontally supporting the tray member in the central chamber and for facilitating at least partial withdrawal of the tray member through the front wall access opening, and means on the tray member for removably holding a plurality of relatively thin rectangular envelopes which contain a substance to be dispensed and which are located in parallel vertical relation to each other to permit air flow past the envelopes from the air inlet chamber to the air outlet chamber.

In one embodiment in accordance with the invention, the housing is portable and additionally includes blower means in one of the air inlet and air outlet chambers for inducing air flow from the air inlet chamber to the central chamber and from the central chamber to the air outlet chamber, and handle means on the housing for facilitating transfer of the housing from one site to another site.

In one embodiment in accordance with the invention, the first partition extends at an angle to the top wall and from adjacent to the corner between the first end wall and the top wall to the second end wall at a point spaced below the top wall, and the second partition extends at an angle to the bottom wall and in generally parallel relation to the first partition from adjacent to the corner between the second end wall and the bottom wall to said first end wall at a point spaced above the bottom wall.

In accordance with one embodiment of the invention, the air inlet means and the air outlet means each comprises a port and the housing is provided with fittings respectively communicating with the air inlet and outlet ports and adapted for connection to duct work.

One of the features of the invention is the provision of an industrial or commercial dispenser for a substance such as a deodorant or odorant.

Another feature of the invention is the provision of a portable dispenser for a substance such as an odorant or deodorant.

Other features and advantages of the invention will become known by reference to the following general description, the claims and accompanying drawings.

THE DRAWINGS

Figure 1:
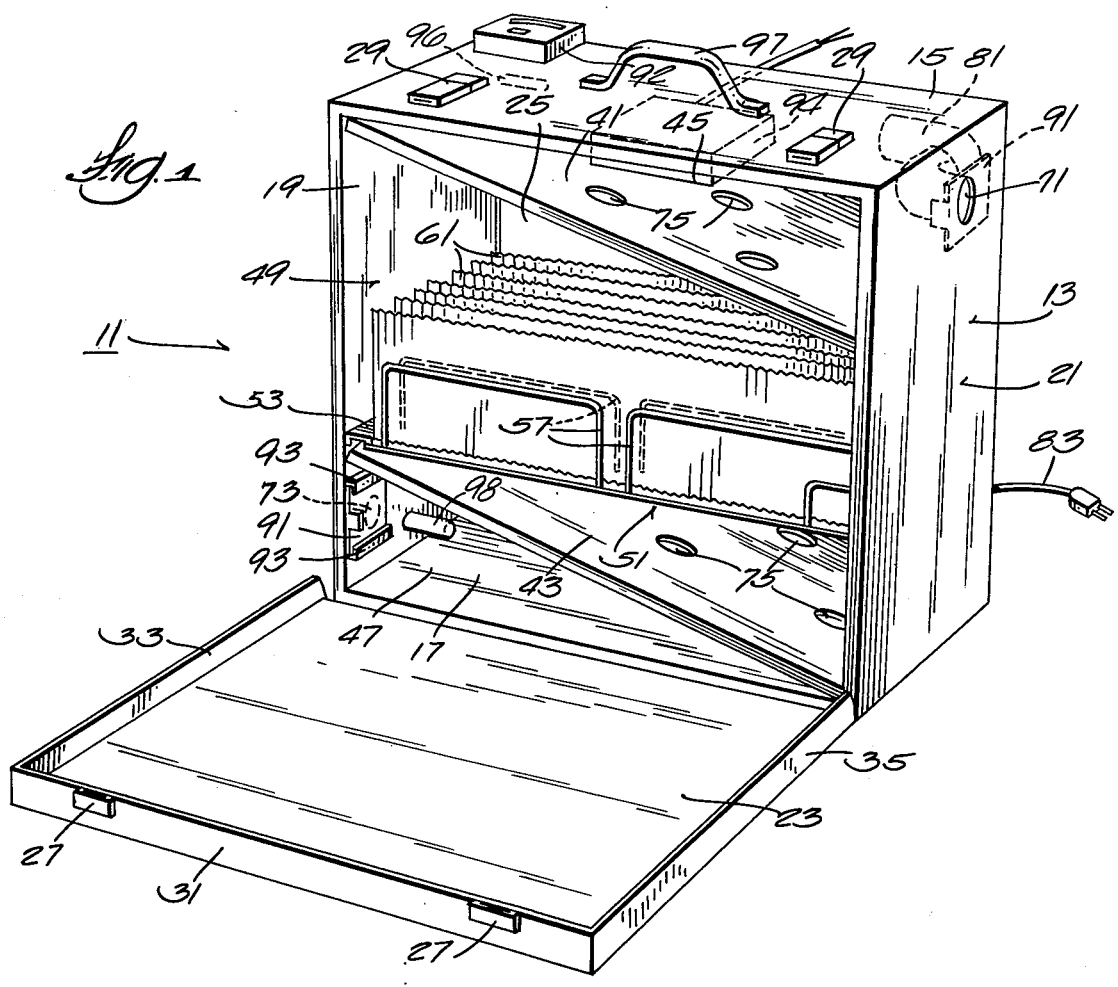
FIG. 1 is a perspective view of a portable dispenser embodying various of the features of the invention.

Before explaining the embodiments of the invention in detail, it is to be understood that the invention is not limited in its application to the details of construction and the arrangement of the components set forth in the following description or illustrated in the drawings. The invention is capable of other embodiments and of being practiced and carried out in various ways. Also, it is to be understood that the phraseology and terminology employed herein is for the purpose of description and should not be regarded as limiting.

GENERAL DESCRIPTION

Shown in FIG. 1 of the drawings is a portable diffuser or dispenser 11 comprising a housing 13 which can be constructed of galvanized sheet metal or other suitable material, which is generally rectangular in shape, and which includes inter-connected top and bottom walls 15 and 17, respectively, opposed first and second or left and right end walls 19 and 21, respectively, and opposed front and rear walls 23 and 25, respectively.

The housing 13 also includes door means providing closable access to the interior of the housing 13. While other arrangements can be employed, in the construction illustrated in FIG. 1, such door means comprises the entire front wall 23 which is hinged to the bottom wall 17 by any suitable means. Means are provided for releasably maintaining the front wall or door 23 in a closed position. While various arrangements can be employed, in the illustrated construction, such means comprises one or more latches including suitable components 27 and 29 located respectively on the front wall or door 23 and on the top wall 15.

The front wall or door 23 also includes top and side flanges 31, 33 and 35 which respectively partially overlie the top wall 15 and the ends walls 19 and 21 when the door 23 is closed so that the housing 13 is substantially air tight. If desired, a suitable gasket (not shown) can be employed.

Located within the housing 13, in generally parallel relation to each other, are first and second or upper and lower partitions 41 and 43. The upper partition 41 extends from the corner between the end walls 19 and top wall 15 at an acute angle to the top wall 15 to the other end wall 21 at a point spaced below the top wall 15 and between the front and rear walls 23 and 25 so as to define an air inlet chamber 45.

The lower partition 43 extends from the corner between the end wall 21 and the bottom wall 17 at an acute angle to the bottom wall 17, and to the other end wall 19 at a point spaced above the bottom wall 17 and between the front and rear walls 23 and 25 so as to define an air outlet chamber 47.

The area between the partitions 41 and 43 comprises a central chamber 49.

Located in the central chamber 49 are one or more tray members or baskets 51 which can be contructed of wire-like material, which are movably supported by suitable guides 53 on the end walls 19 and 21 in generally horizontal relation, i.e., in parallel relation to the top and bottom walls 15 and 17, for movement between a first or interior position completely within the housing 13 and a second position at least partially removed or withdrawn from the housing 13 to facilitate refilling of the tray member or basket 51.

The tray member or basket 51 includes an open mesh bottom and a series of upstanding wire-like guides or posts 57 which are adapted to retain therebetween a series of packages or envelopes 61 which contain a substance to be dispensed, such as, for instance, a deodorant or odorant, and which are supported in an upright and parallel relation to each other. The packages are preferably of thin and flat construction and have corrugated surfaces such as are disclosed in the U.S. Watkins Pat. No. 3,885,737 granted May 27, 1975, thereby to provide a relatively large surface area from which the substance to be dispensed can evaporate in response to air flow past and between the packages 61.

Air flow through the central chamber 49 is provided by means including an air inlet opening or port 71 commmunicating with the air inlet chamber 45 and the atmosphere surrounding the housing 13 and preferably located in the end wall 21, together with an air outlet opening or port 73 communicating with the air outlet chamber 47 and the surrounding atmosphere and preferably located in the opposite end wall 19.

In addition, the first and second partitions 41 and 43 are each preferably provided with a series of apertures 75 affording air flow from the air inlet chamber 45 to the central chamber 49 and from the central chamber 49 to the air outlet chamber 47. The apertures 75 are preferably sized and arranged so that in cooperation with the inclined disposition of the partitions 41 and 43, there is provided a substantially uniform air flow through the central chamber 49 from the air inlet chamber 45 to the outlet chamber 47.

Means are provided for controlling the dispensing rate of the substance to be dispensed. Such means includes the construction of the baskets 51 which permit variance in number of packages 61 supported thereon. In addition, such control means can include means for controlling the rate of air flow through the housing. In this regard, in the construction shown in FIG. 1, the housing 13 also includes an electric blower 81 (shown schematically) which can be located either adjacent to the inlet port 71 to blow air through the housing 13 or adjacent to the outlet port 73 to suck air through the housing 13. In the illustrated construction, the blower 81 is located in the air inlet chamber 45 in adjacent relation to the air inlet port 71 and includes an electric cord 83 which extends from the housing 13 and is adapted to be plugged into a suitable source of electric current to energize the blower 81. If desired an off/on switch can be included in the cord 83 extending from the housing, or as hereinafter disclosed. In addition, it is preferred to employ a gasket (not shown) about the cord 83 at the point where the cord passes through the wall of the housing 13 so as to retain the substantially airtight condition of the housing 13.

In order to control the air flow and thus the rate at which the substance is dispensed and in order to maintain the housing airtight when the blower 81 is not energized, it is preferable to provide each of the inlet and outlet ports 71 and 73 with respective valve means operable to selectively open and close the inlet and outlet ports 71 and 73. While various arrangements can be employed, in the illustrated construction, each such means comprises a sliding plate 91 mounted in guide ways 93 on the associated side wall for movement between a position clear of the associated port and a position closing the associated port. Suitable means (not shown) can be employed for releasably fixing the valve plates 91 in either of their positions.

Still further, the control means can include timer means for controlling the length of the intervals during which the blower 81 is operated and for accumulating and displaying the total time of blower operation. Thus, in the construction shown in FIG. 1, there is schematically shown a combined time-in-use meter and control 92 including a switch (not shown) controlling energization of the blower 81.

The means for controlling the rate at which the substance is dispensed can also include temperature control and heating means for maintaining a minimum temperature in the housing 13. Thus, the construction illustrated in FIG. 1 can also include an electric heating coil 94 and a thermostatic switch 96 (both shown schematically) which energizes the heating coil 94 whenever the temperature drops below a pre-determined level.

Still further the means for controlling the rate at which the substance is dispensed can include a variable pressure-air-flow sensing meter 98 (shown schematically which can include a dial or indicator and which can be employed, in conjunction which appropriate motors for the plates or valves 91 to control the opening and closing thereof in order to more or less maintain a given air flow.

All of the above control means can be used together with each other or less than all can be employed for controlling the rate at which the substance is dispensed.

The dispensing rate can also be controlled by means responsive to variation in the concentration of malodors in the environment into which the substance is dispensed. In such instances, a suitable detection instrument (not shown) can be suitably located in the environment to sense undesirable concentrations of contaminants in the atmosphere and to send a signal to a control means such as a stepping motor connected to the inlet and outlet valves so as to open and close the valves depending upon the signal from the detection instrument. Thusly, the amount of the substance delivered to the environment would be dependent upon the presence of undesirable concentrations of odoriferour contaminants.

The housing 13 shown in FIG. 1 is also provided with a suitable handle 97 which is connected to the top wall 15 and which facilitates removal of the dispenser 11 from one site to another.

In use, the dispenser 11 can be moved from one site to another. When located at the desired site, the valve plates 91 can be opened and the blower 81 connected to source of current so as to flow air past the envelopes or packages 61 and thereby to dispense the substance into the atmosphere adjacent to the outlet port 73. When necessary, the front wall or door 23 can be opened to facilitate movement of the tray member or basket 51 to an extended position so as to facilitate replacement of expended packages 61. When not in use, the front wall or door 23 is closed, as are the valve plates 91 so that the housing is substantially airtight, whereby to substantially preclude undesired loss of the substance from the housing 13.

Figure 2:
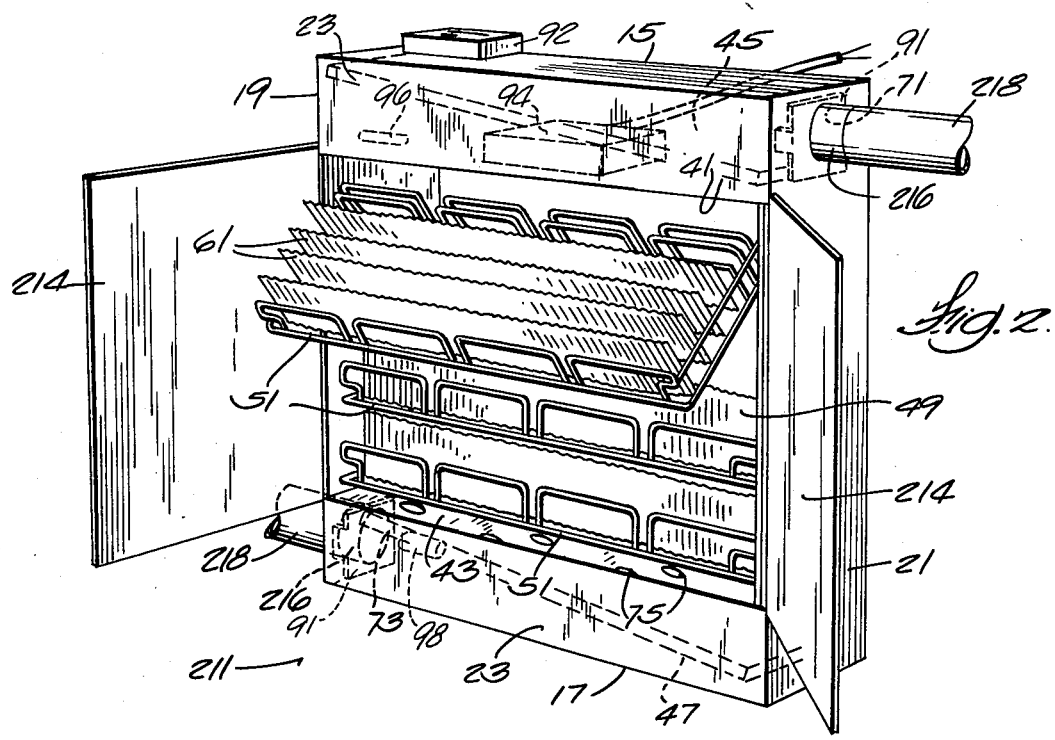
FIG. 2 is a perspective view of a stationary dispenser embodying various of the features of the invention.

Shown in FIG. 2 is another dispenser 211 which is larger as compared to the dispenser 11 shown in FIG. 1 and which is intended to be stationary as distinguished from being portable. As the dispenser 211 is constructed essentially in the same manner as the dispenser 11, except as noted below, the same reference numerals have been applied to the components of the dispenser 211 which are comparable to the components of the dispenser 11.

The dispenser 211 differs from the dispenser 11 in that the dispenser 211 is larger and is adapted to support a series or plurality of tray members or baskets 51 for movement between interior positions and at least partially extending positions affording refilling of the trays or baskets with new packages 61 containing the substance to be dispensed. In addition, the front wall 23 includes two doors 214 which can be opened and closed to provide a closable access opening.

Still further and in addition, the outlet and inlet ports 71 and 73 both include fittings 216 permitting attachment to pipes or ducts 218 so that fresh air can be delivered from a remote spot to the dispenser 211 and so that air containing the dispensed substance can be delivered to remote spots. With such an installation, a blower can alternatively be provided in the duct work as compared to being located in the dispenser 211. In operation, the doors may be opened and the packages replaced when necessary. In addition, any suitable control can be employed for the blower to induce air flow through the dispenser 211.

The dispenser 211 may be provided with all or less than all of the control means described with respect to the dispenser 11.

Various of the features of the invention are set forth in the following claims.

What is claimed is:

1. A vapor dispenser comprising a rectangular housing including interconnected top and bottom walls, opposed front and back walls, opposed first and second end walls, door means in said front wall for providing an access opening which can be opened and closed, a first partition extending in spaced relation to said top wall and between said end walls and between said front and back walls to define an air intake chamber between said first partition and said top wall, air inlet means communicating with said air inlet chamber, a second partition extending in spaced relation to said bottom wall and in generally parallel relation to said first partition and between said end walls and between said front and back walls to define an air outlet chamber between said second partition and said bottom wall and to define a central chamber between said first and second partitions, air outlet means communicating with said air outlet chamber, aperture means in said first and second partitions for affording air flow from said air inlet chamber to said central chamber and from said central chamber to said air outlet chamber, at least one tray member, means on said first and second end walls for horizontally supporting said tray member in said central chamber and for facilitating at least partial withdrawal of said tray member through said front wall access opening and means on said tray member for removably holding a plurality of relatively thin rectangular envelopes which contain a vaporizable substance to be dispensed as a vapor into the flow of air and which are arranged in parallel vertical relation to each other to permit air flow past said envelopes from said air inlet chamber to said air outlet chamber.

2. A dispenser in accordance with claim 1 and including control means, in addition to said tray member, for controlling the rate at which the substance is dispensed.

3. A dispenser in accordance with claim 2 wherein said control means comprises means for maintaining a minimum temperature in said housing.

4. A dispenser in accordance with claim 2 wherein said control means comprises valve means for opening and closing said air inlet and outlet means.

5. A dispenser in accordance with claim 2 wherein said control means comprises time-in-use meter means.

6. A dispenser in accordance with claim 2 wherein said control means comprises a blower for supplying air through said housing.

7. A dispenser in accordance with claim 6 wherein said control means comprises timer means for controlling said blower.

8. A dispenser in accordance with claim 2 wherein said control means comprises variable air flow sensing means.

9. A dispenser in accordance with claim 8 wherein said control means also includes valve means for opening and closing said inlet and outlet means, and means for opening and closing said valve means responsive to said air flow sensing means.

10. A dispenser vapor comprising a rectangular housing including interconnected top and bottom walls, opposed front and back walls, opposed first and second end walls, door means in said front wall for providing an access opening which can be opened and closed, a first partition extending at an angle to said top wall and from adjacent to the corner between said first end wall and said top wall to said second end wall and between said front and back walls to define an air intake chamber between said first partition and said top wall, valved air inlet means in said second end wall communicting with said air inlet chamber, a second partition extending at an angle to said bottom wall and in generally parallel relation to said first partition from adjacent to the corner between said second end wall and said bottom wall to said first end wall and between said front and back walls to define an air outlet chamber between said second partition and said bottom wall and to define a central chamber between said first and second partitions, valved air outlet means in the first end wall communicating with said air outlet chamber, aperture means in said first and second partitions for affording air flow from said air inlet chamber to said central chamber and from said central chamber to said air outlet chamber, at least one tray member, means on said first and second end walls for horizontally supporting said tray member in said central chamber and for facilitating at least partial withdrawal of said tray member through said front wall access opening, means on said tray member for removably holding a plurality of relative thin rectangular envelopes which contain a vaporizable substance to be dispensed as a vapor into the flow of air and which are arranged in parallel vertical relation to each other to permit air flow past said envelopes from said air inlet chamber to said air outlet chamber, blower means in one of said air inlet and air outlet chambers for inducing air flow from said air inlet chamber to said central chamber and from said central chamber to said air outlet chamber, and handle means on said housing for facilitating transfer of said housing from one site to another site.

11. A vapor dispenser comprising a rectangular housing including interconnected top and bottom walls, opposed front and back walls, opposed first and second end walls, door means in said front wall for providing an access opening which can be opened and closed, a first partition extending in spaced relation to said top wall and between said end walls and between said front and back walls to define an air inlet chamber between said first partition and said top wall, an air inlet port communicating with said air inlet chamber, a second partition extending in spaced relation to said bottom wall and in generally parallel relation to said first partition and between said end walls and between said front and back walls to define an air outlet chamber between said second partition and said bottom wall and to define a central chamber between said first and second partitions, an air outlet port communicating with said air outlet chamber, fittings respectively communicating with said inlet and outlet ports and adapted for connection to duct work, aperture means in said first and second partitions for affording air flow from said air inlet chamber to said central chamber and from said central chamber to said air outlet chamber, at least one tray member, means on said first and second end walls for horizontally supporting said tray member in said central chamber and for facilitating at least partial withdrawal of said tray member through said front wall access opening, and means on said tray member for removably holding a plurality of relatively thin rectangular envelopes which contain a vaporizable substance to be dispensed as a vapor into the flow of air and which are arranged in parallel vertical relation to each other to permit air flow past said envelopes from said air inlet chamber to said air outlet chamber.

12. A dispenser in accordance with claim 11 and including control means, in addition to said tray member, for controlling the rate at which the substance is dispensed.

13. A dispenser in accordance with claim 12 wherein said control means comprises means for maintaining a minimum temperature in said housing.

14. A dispenser in accordance with claim 12 wherein said control means comprises valve means for opening and closing said air inlet and outlet ports.

15. A dispenser in accordance with claim 12 wherein said control means comprises time-in-use meter means.

16. A dispenser in accordance with claim 12 wherein said control means comprises a blower for supplying air through said housing.

17. A dispenser in accordance with claim 16 wherein said control means comprises timer means for controlling said blower.

18. A dispenser in accordance with claim 12 wherein said control means comprises variable air flow sensing means.

19. A dispenser in accordance with claim 18 wherein said control means also includes valve means for opening and closing said inlet and outlet ports, and means for opening and closing said valve means responsive to said air flow sensing means.

20. A vapor dispenser comprising a rectangular housing including interconnected top and bottom walls, opposed front and back walls, opposed first and second end walls, door means in said front wall for providing an access opening which can be opened and closed, a first partition extending in spaced relation to said top wall and between said end walls and between said front and back walls to define an air inlet chamber between said first partition and said top wall, an air inlet port communicating with said air inlet chamber, a second partition extending in spaced relation to said bottom wall and between said end walls and between said front and back walls to define an air outlet chamber between said second partition and said bottom wall and to define a central chamber between said first and second partitions, an air outlet port communicating with said air outlet chamber, aperture means in said first and second partitions for affording air flow from said air inlet chamber to said central chamber and from said central chamber to said air outlet chamber, at least one tray member, means on said first and second end walls for horizontally supporting said tray member in said central chamber and for facilitating at least partial withdrawal of said tray member through said front wall access opening, and means on said tray member for removably holding a plurality of relatively thin rectangular envelopes which contain a vaporizable substance to be dispensed as a vapor into the flow of air and which are arranged in parallel vertical relation to each other to permit air flow past said envelopes from said air inlet chamber to said air outlet chamber.

* * * * *